United States Patent [19]

Thomas

[11] Patent Number: 4,523,022

[45] Date of Patent: Jun. 11, 1985

[54] ANALOGS OF THE ANTIBIOTIC SPECTINOMYCIN

[75] Inventor: Richard C. Thomas, Oshtemo Township, Kalamazoo County, Mich.

[73] Assignee: The Upjohn Company, Kalamazoo, Mich.

[21] Appl. No.: 511,802

[22] Filed: Jul. 7, 1983

[51] Int. Cl.$^3$ .................................... C07D 313/02
[52] U.S. Cl. ........................... 549/354; 549/361; 549/332
[58] Field of Search ........................... 549/354, 361

[56] References Cited

U.S. PATENT DOCUMENTS

| | | | |
|---|---|---|---|
| 3,234,092 | 2/1966 | Bergy et al. | 424/116 |
| 4,173,647 | 11/1979 | Maier et al. | 549/361 |
| 4,351,771 | 9/1982 | White | 549/361 |
| 4,361,701 | 11/1982 | White | 549/361 |

FOREIGN PATENT DOCUMENTS

| | | |
|---|---|---|
| 2756912 | 7/1979 | Fed. Rep. of Germany . |
| 2756913 | 7/1979 | Fed. Rep. of Germany . |

OTHER PUBLICATIONS

Boissonnas, Adv. Org. Chem. 3, 159–190 (1963).
Windholz et al., Tetrahedron lett., 8, 2555 (1967).
Wiley et al., J. Am. Chem. Soc. 85, 2652 (1963).
Knight and Hoeksema, J. Antibiotics 28, 136 (1975).
Smith et al., Chap. II, "The Demjanov and Tiffeneau–Demjanov Ring Expansions", Organic Reactions, Wiley, N.Y., 1960, pp. 157–188.
H. Soll, "Methoden Der Organischen Chemie", vol. 11(2), 4th Edition, Gearg Thieme Verlag, Stuttgart, 1958, pp. 133–172.
C. D. Gutsche et al., Chapter IV, "Diazoalkane Ring Expansions of Cycloalkanones", Carbocyclic Ring Expansion Reactions, Academic Press, N.Y., 1968, pp. 81–98.
European Application Serial No. 82 305 299,8, (Publication No. 0079125).

*Primary Examiner*—Nicky Chan
*Attorney, Agent, or Firm*—Joan Thierstein

[57] ABSTRACT

The present invention concerns the novel, sugar-ring expansion for synthesis of novel analogs of spectinomycin or C-6' analogs of spectinomycin from known aminomethyldihydrospectinomycin and analogs thereof. Additionally, the invention concerns the novel synthesis of novel 7 membered sugar-ring analogs of dihydrospectinomycin and C-6' analogs thereof from novel 7 membered sugar-ring spectinomycin and C-6' analogs thereof by treatment with NaBH$_4$.

7 Claims, No Drawings

ANALOGS OF THE ANTIBIOTIC SPECTINOMYCIN

DESCRIPTION

Technical Background

1. Field of the Invention

The present invention relates to novel compounds and processes. In particular, the invention relates to novel analogs of the aminocyclitol antibiotic spectinomycin and novel processes having additional selected novel analogs as intermediates for synthesizing the novel analogs.

The novel analogs of spectinomycin disclosed herein are useful as antimicrobial agents.

Spectinomycin is the compound illustrated, with numbering of carbon positions, in formula I.

The present invention relates to novel expanded 7 membered sugar-ring analogs of
(i) spectinomycin (formula I),
(ii) C-6' analogs of spectinomycin, including the 5'-desmethyl analog, of spectinomycin illustrated in formula $I_1$ wherein $R_4$ is:
  (a) hydrogen
  (b) alkyl of 2 to 8 carbon atoms, inclusive,
  (c) $—R_{31}—O—R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
  (d) $—R_{31}—NR_{33}R_{34}$, wherein $R_{31}$ is as defined above, wherein $R_{33}$ is hydrogen or alkyl of 1 to 6 carbon atoms, inclusive, and wherein $R_{34}$ is hydrogen, alkyl of 1 to 6 carbon atoms, inclusive, or a blocking group with the proviso that when $R_{34}$ is not a blocking group, the sum of (a) the number of carbon atoms in $R_{31}$ and (b) the number of carbon atoms in whichever of $R_{33}$ or $R_{34}$ has the larger number of carbon atoms is less than or equal to 7, or
  (e) alkyl of 1 to 4 carbon atoms, inclusive, substituted with 1, 2, or 3 halogen atoms,
(iii) C-6' analogs of dihydrospectinomycin, illustrated in formula $I_2$ wherein $R_3$ is:
  (a) hydrogen
  (b) alkyl of 1 to 8 carbon atoms, inclusive,
  (c) $—R_{31}—O—R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
  (d) $—R_{31}—NR_{33}R_{34}$, wherein $R_{31}$ is as defined above, wherein $R_{33}$ is hydrogen, alkyl of 1 to 6 carbon atoms, inclusive, and $R_{34}$ is hydrogen, alkyl of 1 to 6 carbon atoms, inclusive, or a blocking group with the proviso that if $R_{34}$ is not a blocking group, the sum of the number of carbon atoms in $R_{31}$ and the number of carbon atoms in whichever of $R_{33}$ or $R_{34}$ has the larger number of carbon atoms is less than or equal to 7, or
  (e) alkyl of 1 to 4 carbon atoms, inclusive, substituted with 1, 2 or 3 halogen atoms,
(iv) analogs of spectinomycin (formula I), C-6' analogs thereof (formula $I_1$), and C-6' analogs of dihydrospectinomycin (formula $I_2$) in which the hydrogen atoms attached to each of the nitrogen atoms bonded to C-1 and C-3 in the molecules are replaced by a blocking group.

Unless otherwise qualified, reference herein to an expanded 7 membered sugar-ring analog of spectinomycin or C-6' analogs of spectinomycin includes references to the aforementioned analogs with the nitrogen atoms bonded to C-1 and C-3 blocked and to analogs of dihydrospectinomycin and C-6' analogs of dihydrospectinomycin (including C-6' analogs with nitrogen atoms bonded to C-1 and C-3 blocked).

Blocking groups as referred to above are sometimes called "protective groups" in the art and are well known in many fields of organic chemistry, including peptide chemistry, fatty acid chemistry and especially semi-synthetic and synthetic antibiotic chemistry. Two commonly used blocking groups are carbobenzyloxy and t-butoxycarbonyl. Such groups can be removed easily and replaced by hydrogen atoms with suitable treatments, which may vary in detail depending on the particular blocking group and the particular molecule to which it is bonded, with acids or by reduction. A quite comprehensive list of blocking groups which can be attached to spectinomycin analogs is disclosed in U.S. Pat. No. 4,173,647, the selection, preparation, use and removal of which is incorporated herein by reference. Regarding the chemistry of adding and removing such blocking groups, see, e.g., Boissonnas, Adv. Org. Chem. 3, 159 to 190 (1963) and Windholz et al., Tetrahedron Lett., 8, 2555 (1967).

Spectinomycin itself is a known natural product. See Bergy et al., U.S. Pat. No. 3,234,092. Numerous spectinomycin analogs in which the nitrogen atom bonded to C-1 and C-3 are blocked are also known. See White, inventor of both, U.S. Pat. Nos. 4,351,771 and 4,361,701; Federal Republic of Germany Offenlegungsschriften No. 2,756,912 (Derwent Farmdoc Accession No. 50959B) and No. 2,756,913 (Derwent Farmdoc Accession No. 40960B). The White patents include numerous C-6' analogs including the 5'-desmethyl, of spectinomycin as well as such analogs with nitrogen atoms bonded to C-1 and C-3 blocked.

The present invention also concerns novel synthetic processes. In particular, it concerns:
(i) the novel, sugar-ring expansion for synthesis of novel analogs of spectinomycin or C-6' analogs of spectinomycin from known aminomethyldihydrospectinomycin and analogs thereof described in European application Ser. No. 82 305 299.8 having as priority U.S. application Ser. No. 417,313, filed Sept. 13, 1982, now U.S. Pat. No. 4,465,848, a continuation-in-part of U.S. Ser. No. 314,261, filed Oct. 23, 1981 now abandoned;
(ii) the novel synthesis of novel 7 membered sugar-ring analogs of dihydrospectinomycin and C-6' analogs thereof from novel 7 membered sugar-ring spectinomycin and C-6' analogs thereof by treatment with NaBH$_4$, or other reducing agents such as hydrogen in the presence of platinum, nickel or another metal catalyst.

With respect to novel process (ii), the stereochemistry of the new asymmetric center at C-3' is not determined.

All of the analogs of the present invention which contain one or more blocking groups, and all of the analogs which contain a keto group at C-3', are useful intermediates in processes for making C-3' analogs of the 7 membered sugar-ring analogs of spectinomycin which are also useful as antimicrobial agents by reduction of the keto to the corresponding dihydro analog.

The present invention also includes the pharmacologically acceptable acid addition salts of the novel antimicrobial expanded 7 membered sugar-ring analogs of spectinomycin disclosed herein.

Similar to the known antimicrobial aminomethyldihydrospectinomycin and C-6' analogs of aminomethyldihydrospectinomycin which are precursors herein, the novel expanded 7 membered sugar-ring spectinomycin analogs of the present invention are useful as antimicrobial agents, i.e., are either microbistatic or microbicidal. The novel antimicrobial expanded 7 membered sugar-ring spectinomycin analogs within the scope of the present invention are useful for inhibiting the growth of, or eliminating, microorganisms in various environments wherein the presence or unchecked growth of the microorganism is undesirable or harmful. Each of the antimicrobial expanded 7 membered sugar-ring spectinomycin analogs of the present invention is microbistatic or microbicidal against at least one microorganism in at least one environment in which the presence of the microorganism is undesirable or harmful. Microorganisms against which at least one of the antimicrobial expanded 7 membered sugar-ring spectinomycin analogs of the present invention are active include *E. coli, K. pneumoniae, S. marcensens, S. typhi, S. faecalis, P. vulgaris, P. mirabilis, Ps. aeruginosa,* as well as others, including both gram-negative and gram-positive bacteria. Some of the novel, antimicrobial expanded 7 membered sugar-ring spectinomycin analogs of the present invention are also useful for treating or preventing microbial infections in mammals, including humans.

Other than well known deprotection reactions required to replace blocking groups with hydrogen atoms on blocked nitrogen atoms, the chemical transformations disclosed in the present specification occur at C-3'. None of the chemical transformations disclosed in the present specification alter the configuration at any chiral center, other than C-3', from the configuration exhibited by spectinomycin, its actinamine-ring-nitrogen-blocked analogs, or any of the C-6' analogs of spectinomycin (including actinamine-ring-nitrogen-blocked) of concern in the present specification as starting materials in the synthesis of the novel expanded 7 membered sugar-ring spectinomycin C-3' analogs. The configuration of the chiral center, at C-3' in the dihydro expanded 7 membered sugar-ring spectinomycin is not known. The configuration about any chiral center that may be present in a blocking group or a substituent at C-6' in the precusor is not changed by any of the chemical transformations disclosed in the present specification.

2. Prior Art

The aminomethyldihydrospectinomycin and analogs thereof, which are the substrate for the ring expansion of the novel process having novel intermediates and novel compounds of the present invention, are described in European patent application No. 82 305 299.8, filed Oct. 5, 1982, having a priority of U.S. application Ser. No. 314,261, filed Oct. 23, 1981 now pending, which is incorporated herein by reference.

There are few references to spectinomycin analogs with modified sugar-rings in the literature, and none of these involve compounds with an expanded 7 membered sugar-ring. For example, see U.S. Pat. Nos. 4,351,771, 4,361,701, and 4,173,647.

Several C-3' analogs of spectinomycin, with and without blocking groups on the actinamine-ring nitrogens (i.e., the nitrogens bonded to C-1 and C-3) are known. In aqueous solution, spectinomycin exists as the C-3' ketone hydrate. Wiley, et al., J. Am. Chem. Soc. 85, 2652 (1963).

Wiley, et al., J. Am. Chem. Soc. 85, 2652 (1963) also report the preparation of both C-3' epimers of 3'-dihydrospectinomycin.

Knight and Hoeksema, J. Antibiotics 28, 136 (1975), disclose the N,N'-di(carbobenzyloxy) derivative of spectinomycin itself and both epimers of the 3'-dihydro analog. (The nitrogen atoms bonded to C-1 and C-3 are designated herein as N and N', respectively).

Numerous analogs of both 3'-epimers of 3'-dihydrospectinomycin are reported in U.S. patent application Ser. No. 020,073, filed Mar. 13, 1979 now U.S. Pat. No. 4,361,701. The analogs include actinamine-ring-nitrogen unblocked and blocked with a wide variety of blocking groups, 5'-desmethyl compounds and compounds substituted at C-6' with a variety of substituents. However, no teaching is present including the expanded 7 membered sugar-ring.

No analogs of spectinomycin appear known to the art wherein the sugar-ring is an expanded 7 membered sugar-ring.

The U.S. Pat. Nos. 4,351,771 and 4,361,701 are references which include spectinomycin analogs with modified sugar-rings; however, the modification is not a ring expansion. It is modification at the C-6' position. Additionally, U.S. application Ser. No. 449,304, filed Dec. 13, 1982, now pending, which is a continuation-in-part of U.S. application Ser. No. 359,723, filed Mar. 19, 1982, describe compounds that are modified at the C-6' position which are more preferred. Again, none of the prior disclosures of the above cited references include a ring expansion of the sugar-ring which are shown in the presence specification.

A review of ring expansion reactions can be found described by H. Soll in *Methoden Der Organischen Chemie,* vol. 11(2), 4th edition, Gearg Thieme Verlag, Stuttgart, 1958, pp. 133, C. D. Gutsche et al. in Chapter IV in "Diazoalkane Ring Expansions of Cycloalkanones", *Carbocyclic Ring Expansion Reactions,* Academic Press, N.Y., 1968, pp. 81–98, and Smith et al., Chapter II in "The Demjanov and Tiffeneau-Demjanov Ring Expansions", *Organic Reactions,* Wiley, N.Y., 1960, pp. 157–188. In view of the high degree of functionality present in the molecule of spectinomycin or its analogs, the water solubility of spectinomycin or its analogs, and the lability of masked α-diketone system at carbons 2' and 3' the three immediately preceding references describing carbocyclic ring expansion reactions provide no basis for making obvious the reaction conditions employed therein to form the spectinomycin analogs having the expanded 7 membered sugar-ring. In fact, there appear to be no examples in the literature to make obvious the 7 membered sugar-ring spectinomycin analog or the microbistatic or the microbicidal activity now found for the expanded sugar-ring analogs of spectinomycin, C-6' analogs of spectinomycin and dihydrospectinomycin of the present invention.

THE INVENTION

1. Summary of the Invention
The present invention comprises:
(A) A compound of formula II,
wherein
$R_1$ is
 (a) hydrogen or (b) a blocking group; and
wherein
$R_3$ is
 (a) hydrogen
 (b) alkyl of 1 to 8 carbon atoms, inclusive,
 (c) $-R_{31}-O-R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
 (d) $-R_{31}-NR_{33}R_{34}$, wherein $R_{31}$ is as defined above, wherein $R_{33}$ is hydrogen, alkyl of 1 to 6 carbon atoms, inclusive, and $R_{34}$ is hydrogen, alkyl of 1 to 6 carbon atoms, inclusive, or a blocking group, with the proviso that if $R_{34}$ is not a blocking group, the sum of the number of carbon atoms in $R_{31}$ and the number of carbon atoms in whichever of $R_{33}$ or $R_{34}$ has the larger number of carbon atoms is less than or equal to 7, or
 (e) alkyl of 1 to 4 carbon atoms, inclusive, substituted with 1, 2, or 3 halogen atoms;
wherein
A is
 (a) =O or
 (b) α-H:β-OH; α-OH:β-H; and pharmacologically acceptable salts thereof.
(B) A process for preparing a compound of formula IIa,
wherein
$R_1$ is
 (a) hydrogen or
 (b) a blocking group; and
wherein
$R_3$ is
 (a) hydrogen
 (b) alkyl of 1 to 8 carbon atoms, inclusive,
 (c) $-R_{31}-O-R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
 (d) $-R_{31}-NR_{33}R_{34}$, wherein $R_{31}$ is as defined above, wherein $R_{33}$ is hydrogen, alkyl of 1 to 6 carbon atoms, inclusive, and $R_{34}$ is hydrogen, alkyl of 1 to 6 carbon atoms, inclusive, or a blocking group, with the proviso that if $R_{34}$ is not a blocking group, the sum of the number of carbon atoms in $R_{31}$ and the number of carbon atoms in whichever of $R_{33}$ or $R_{34}$ has the larger number of carbon atoms is less than or equal to 7, or
 (e) alkyl of 1 to 4 carbon atoms, inclusive, substituted with 1, 2, or 3 halogen atoms;
which comprises
 (a) reacting in an inert solvent a compound of formula IV
wherein $R_1$ is a blocking group and $R_3$ is as defined above; with nitrous acid or alkyl nitrite and recovering a compound having the formula IIa, wherein $R_1$ is a blocking group (Scheme A), or
 (b) reacting in an inert solvent a compound having formula IV
wherein $R_1$ is a blocking group and $R_3$ is as defined above; with nitrous acid or alkyl nitrite and recovering a compound having the formula IIa wherein $R_1$ is a blocking group (Scheme A) and replacing the blocking group $R_1$ with hydrogen (Scheme B).

(C) A process for preparing a compound of formula IIb,
wherein
$R_1$ is
 (a) hydrogen or
 (b) a blocking group; and
wherein
$R_3$ is
 (a) hydrogen
 (b) alkyl of 1 to 8 carbon atoms, inclusive,
 (c) $-R_{31}-O-R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
 (d) $-R_{31}-NR_{33}R_{34}$, wherein $R_{31}$ is as defined above, wherein $R_{33}$ is hydrogen, alkyl of 1 to 6 carbon atoms, inclusive, and $R_{34}$ is hydrogen, alkyl of 1 to 6 carbon atoms, inclusive, or a blocking group, with the proviso that if $R_{34}$ is not a blocking group, the sum of the number of carbon atoms in $R_{31}$ and the number of carbon atoms in whichever of $R_{33}$ or $R_{34}$ has the larger number of carbon atoms is less than or equal to 7, or
 (e) alkyl of 1 to 4 carbon atoms, inclusive, substituted with 1, 2, or 3 halogen atoms;
which comprises
 (a) reacting a compound having the formula IIa wherein $R_1$ is a blocking group and $R_3$ is as defined above with $NaBH_4$ (Scheme C); or
 (b) reacting a compound having the formula IIa wherein $R_1$ is a blocking group and $R_3$ is as defined above with $NaBH_4$ and replacing the blocking group denoted by $R_1$ with hydrogen (Scheme D).

The bivalent substituent herein, i.e. A, may be defined in the form α-H:β-OH or α-OH:β-H wherein either H represents the substituent in the alpha configuration and OH in the beta configuration or H represents the substituent in the beta configuration and OH in the alpha configuration with respect to the plane of the ring to which said substituent is attached.

In other words, the stereochemistry of the new asymmetric center at C-3' has not been determined.

For convenience in assigning trivial names to compounds having the formula II herein, when A is =O, i.e. IIa, the chemical skeleton described when $R_1$ is hydrogen and $R_3$ is methyl shall be referred to as "homospectinomycin". Further when compounds having the formula II herein when A is α-H:β-OH; α-OH:β-H (IIb); the chemical skeleton described when $R_1$ is hydrogen and $R_3$ is methyl shall be referred to as "homodihydrospectinomycin".

The compounds within the scope of the invention are useful as either antimicrobial agents or intermediates in processes for synthesizing antimicrobial agents. The compounds within the scope of the present invention which are antimicrobial agents are the compounds of formula II wherein $R_1$ substituents are not blocking groups and A is =O or α-H:β-OH; α-OH:β-H; and pharmacologically acceptable acid addition salts thereof. The compounds within the scope of the present invention which are useful as intermediates in synthetic processes to make the antimicrobial compounds of the invention are those of formula II wherein $R_1$ are all blocking groups, and A is =O or α-H:β-OH; α-OH:β-H.

The compounds within the scope of the invention which are useful as antimicrobial agents are microbistatic or microbicidal. They can be used to inhibit the growth of, or eliminate, microorganisms, including gram-negative and gram-positive bacteria, from environments in which the presence of microorganisms is undesirable or harmful. While the microbistatic or microbicidal potency of the antimicrobial agents within the scope of the invention will vary against any undesirable or harmful species of microorganisms in a particular environment, each antimicrobial agent within the scope of the invention will be useful against at least one species of microorganisms in at least one environment in which the presence of members of the species is harmful or undesirable.

The antimicrobial agents within the scope of the invention are useful for treating or preventing microbial, especially bacterial, infections in mammals, including humans. Additionally, it is contemplated that the antimicrobial agents within the scope of the present invention will be useful for inhibiting the growth of, or eliminating, microorganisms from environments, other than mammalian systems, in which the presence of the microorganism is undesirable or harmful.

To be effective as microbistatic or microbicidal agents in an environment, the antimicrobial compounds within the scope of this invention must be introduced into the environment, by one of several means which are well known in the art and which are described in more detail below, in a quantity sufficient to inhibit the growth of, or eliminate, the target microorganisms.

2. Detailed Description of the Invention

The illustrative examples below and Charts A through D describe the preparation and use of the novel compounds and processes herein. Variations from the details given herein, e.g., solvent or temperature or other reaction conditions, provided in the discussion and Examples, are also contemplated as part of the invention. The discussion and Examples are intended, therefore, to be illustrative, not comprehensive. Except as otherwise noted, however, the Examples do set forth preferred conditions for the reactions exemplified.

Compounds of formula IV in Scheme A are the starting materials for synthesizing all compounds within the scope of this invention. All compounds of formula IV are known. For such starting materials see European patent application No. 82305299.8, filed Oct. 5, 1982, having as priority the U.S. application Ser. No. 417,313, filed Sept. 13, 1982, now U.S. Pat. No. 4,465,848 which is a continuation-in-part of U.S. application Ser. No. 314,261, filed Oct. 23, 1981 now abandoned. The U.S. Patent application Ser. No. 417,313 and U.S. Patent application Ser. No. 314,261 are incorporated here by reference.

Generally, the ring expansions described in Scheme A are undertaken in the presence of water. Any organic solvent which is inert with the reactants and in which the reactants are soluble may also be present for the formation of the compound of formula IIa from the compound of formula IV. Such solvents include, for example, acetic acid, dimethyl ether, diethyl ether, tetrahydrofuran. The preferred solvent is aqueous acetic acid.

The ring expansion is accomplished by treating the formula IV compound with nitrous acid or alkyl nitrite. The nitrous acid may be generated from sodium nitrite, potassium nitrite, or silver nitrite; as well as other sources of nitrite ion, such as alkyl nitrites, e.g., isoamyl nitrites, treated with acetic acid, formic acid, hydrochloric acid, sulfuric acid, and the like. The usual temperatures for the treatment of compounds having IV range from 0° to 100° C., with 0° to 25° C. being preferred. Such treatment leads to the formation of three products in roughly equal amounts. These are shown in Scheme A as compounds having V, VI, and IIa (wherein $R_1$ is a blocking group).

After careful chromatography, the compounds are separated and identified as compounds having the formula V and VI with the use of $^{13}$C-NMR spectra and TLC mobilities, and the major product having the formula IIa (wherein $R_1$ is a blocking group). On the basis of its $^{13}$C-NMR and mass spectrum, this product is identified as having the expanded 7 membered sugar-ring shown in formula IIa (wherein $R_1$ is a blocking group). Deprotection of compounds having the formula IIa as shown in Scheme B is accomplished under standard conditions known in the art and as disclosed in the various previously disclosed reference describing modified spectinomycin compounds.

For example, compounds having the formula IIa (wherein $R_1$ is a benzyloxycarbonyl group) may be treated with formic acid in the presence of palladium and hydrochloric acid to obtain the dihydrogen chloride salt of compounds having the formula IIa (wherein $R_1$ is hydrogen). No evidence for a ketone hydrate of the carbonyl group at the C-3′ position which is anticipated for compounds having the structure formula IIa is shown and is noteworthy in the deprotection by the method of this example. In other words, the lack of hydration at the C-3′ ketone in compounds having the formula IIa (wherein $R_1$ is hydrogen) is surprising in light of total hydration of the analogous deprotection of parent six member ring containing compounds.

Further utility of the ring expanded compound having the formula IIa (wherein $R_1$ is a blocking group) from the preparation of Scheme A is shown in Scheme C. It is readily seen the ketone functional group at C-3′ in the compound having the formula IIa (wherein $R_1$ is a blocking group) is reduced to obtain a compound previously referred to generally as a "homodihydrospectinomycin", which is analogous to that of the parent dihydrospectinomycin prepared in U.S. Pat. No. 4,361,701, referred to above.

The reduction shown in Scheme C is again carried out in any organic solvent in which the reactants are soluble. Such solvents include, for example, tetrahydrofuran, methanol, ethanol and the like. The preferred solvent is ethanol. To the solution of the compound having the formula IIa (wherein $R_1$ is a blocking group) is added sodium borohydride ($NaBH_4$). Generally, temperatures between 0° C. and 60° C. are acceptable. Preferred temperatures are 20°–30° C.

The reactions above are carried out with nitrogen atoms in the spectinomycin moiety blocked or unblocked. Preferably, the nitrogens are blocked as shown in Schemes A through D, most preferably, with carbobenzyloxy or t-butoxycarbonyl.

Again "blocking groups" are removed from the compounds having the formula IIb as shown in Scheme D. Those skilled in the art will readily recognize how to modify reaction conditions from those provided in the examples to add and remove blocking groups other than those for which conditions are specifically exemplified. In this specification, "blocking group" and "protecting group" are synonymous, as are "block" and "protect", and "deblock" and "deprotect." Preferred blocking groups in all reactions within the scope of the present invention is carbobenzyloxy.

When deblocking leads directly to an acid addition salt, the free base can be generated from such salt by methods well known in the art, e.g., passing a solution of the salt in a solvent such as water, methanol, ethanol, tetrahydrofuran, 1,2-dimethoxyethane or the like through a basic ion exchange resin and collecting fractions of eluate which contain the free base.

Pharmacologically acceptable acid addition salts can be produced from the free bases by methods well known in the art, e.g., neutralizing the free base in solution in a solvent such as water, methanol, ethanol, isopropanol, ether, 1,2-dimethoxyethane, p-dioxane or the like with any acid which has a pharmacologically acceptable conjugate base and then isolating the salt by filtration and direct crystallization or by evaporation of solvent followed by subsequent recrystallization from a suitable solvent. Acids which have pharmacologically acceptable conjugate bases include hydrochloric, hydrobromic, hydroiodic, sulfuric, phosphoric, maleic, citric, tartaric, fumaric, acetic, and the like. Especially preferred among the pharmacologically acceptable acid addition salts within the scope of the present invention is hydrochloric.

Preferred antimicrobial agents within the scope of the present invention are compounds of formula IIa wherein $R_3$ is alkyl of 1 to 4 carbon atoms, inclusive. Especially preferred are such compounds wherein $R_3$ is methyl or butyl.

The compounds of formula II are useful either as intermediates in processes to synthesize antimicrobial agents or as antimicrobial agents.

The compounds of formula II which contain one or mre blocking groups or wherein A is =O are useful as intermediates in processes to synthesize compounds within the scope of the present invention which are antimicrobial agents.

The compounds of formula II which contain no blocking groups and wherein A is $\alpha$-H:$\beta$-OH; $\alpha$-OH:$\beta$-H are also antimicrobial agents.

The antimicrobial agents within the scope of the present invention inhibit the growth of, or eliminate microorganisms in various environments where the presence of microorganisms is undesirable or harmful.

The antimicrobial activity of compounds within the scope of the invention is determined by a serial-dilution technique whereby, for each of several species of microorganisms the minimum concentration of a compound required to prevent an increase in the concentration of cells in an inoculum containing a known initial concentration of cells in a growth phase is determined.

Based on results with the technique applied to the known antibiotic, spectinomycin dihydrochloride, a compound is judged active against species of microorganisms if its "minimum inhibitory concentration" against the microorganism using the technique is less than 250 mcg/ml. By this criterion, all of the antimicrobial compounds within the scope of the invention were found to be active against at least one of the following species of microorganisms:
*Staphyloccus aureus*
*Streptococcus faecalis*
*Eshericia coli*
*Klebsiella pneumoniae*
*Pseudomonas aeruginosa*
*Proteus vulgaris*
*Proteus mirabilis*
*Shigella flexneri*
*Salmonella typhi*
*Serratia marcescens*
*Providencia stuartii*

Minimum inhibitory concentrations (in mcg/ml) for several antimicrobial compounds within the scope of the invention are provided in the following Chart:

| CHART | | A | B | C |
|---|---|---|---|---|
| *Staphylococcus aureus* | (UC #76) | 80 | 10 | 20 |
| *Streptococcus faecalis* | (UC #694) | >160 | 40 | 160 |
| *Escherichia coli* | (UC #45) | 40 | 5 | 10 |
| *Klebsiella pneumoniae* | (UC #58) | 40 | 2.5 | 5 |
| *Pseudomonas aeruginosa* | (UC #95) | >160 | 20–40 | 80 |
| *Proteus vulgaris* | (UC #93) | >160 | 10–20 | 80 |
| *Proteus mirabilis* | (UC #6671) | 160 | 10 | 40 |
| *Shigella flexneri* | (UC #143) | 40 | 10 | 10 |
| *Salmonella typhi* | (UC #215) | 40 | 5 | 5 |
| *Serratia marcescens* | (UC #131) | 80 | 5 | 20 |
| *Providencia stuartii* | (UC #6570) | >160 | >160 | >160 |

A: Homodihydrospectinomycin
B: Spectinomycin dihydrochloride tetrahydrate (control) (Ranges reflect value obtained on different days)
C: Homospectinomycin Antimicrobial compounds with the scope of the present invention are active against *E. coli* and can be used, for example, to reduce, arrest and eradicate slime production in papermill systems caused by this microorganism. The antimicrobial compounds can also be used to prolong the life of cultures of *Trichomonas foetus*, *Trichomonas hominis* and *Trichomonas vaginalis* by freeing them of *E. coli* contamination. The antimicrobial compounds can be used to swab laboratory benches and equipment in mycological laboratories. The antimicrobial compounds can also be used effectively against *K. pneumoniae*.

To be used as suggested as above, the antimicrobial compounds of the present invention are incorporated into solutions, powders, suspensions, water-in-oil emulsions and like means of delivery which are well known and are described in greater detail below in connection with administration to mammals and humans. The concentration of antimicrobial compound in these means of delivery or application must be at least sufficient to inhibit the growth of target microorganisms at site of application. These minimum effective concentrations will vary, depending on the target microorganism, the environment in which its growth is to be slowed or it is to be eliminated, and the particular means of delivery used. The minimum effective concentration could be determined readily by a person skilled in the art. It is contemplated that the minimum effective concentration will range from about 1 part per million to about 10,000 parts per million, preferably 10 parts per million to 1000 parts per million in the solution, powder, suspension or emulsion. The preferred carrier is water.

The antimicrobial compounds within the scope of the present invention are useful for treating or preventing microbial infections, particularly bacterial infections, in mammals, including humans, suffering from or susceptible to such infections. The antimicrobial activity of a compound in mammals, including humans, is suggested by a minimum inhibitory concentration in the in vitro test described above of less than about 50 μg/ml against a microorganism. The antimicrobial activity of a compound against a microorganism in mammals, including humans, is ascertained more definitely by testing the ability of the compound to cure mammals, such as mice, rats or rabbits, which have been challenged with an acute dose of the microorganism.

The compounds of formula II are also effective for treating bacterial infections, such as gonorrhea, in mammals, including humans.

The compositions of the present invention are presented for administration to humans and animals in unit dosage forms, such as tablets, capsules, pills, powders, granules, sterile parenteral solutions or suspension, eye drops, oral solutions or suspensions, and water-in-oil emulsions containing suitable quantities of the compound of formula II.

For oral administration, either solid or fluid unit dosage forms can be prepared. For preparing solid compositions such as tablets, the compound of formula II is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparation solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1–2.5 gm.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such as active material for use in humans and animals, as disclosed in detail in this specification, these being features of the present invention. Examples of suitable unit dosage forms in accord with this invention are tablets, capsules, pills,, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans of from about 2 to about 4000 mg of compound in a single dose, administered parenterally or in the compositions of this invention, are effective for treating bacterial infections. More specifically, the single dose is from 5 mg to about 5000 mg in a single dose. More specifically, the dose is from about 10 mg to about 2500 mg of compound.

3. Examples

The following examples are indicative of the scope of this invention but are not to be construed to be limitative. Those skilled in the art will recognize appropriate variations from the processes both as to precursors as well as reaction conditions and techniques.

The operation of the present invention is particularly illustrated by the examples below:

EXAMPLE 1

N,N'-dibenzyloxycarbonylhomospectinomycin (formula IIa: $R_3$ is methyl and $R_1$ is carbobenzyloxy)

Refer to Scheme A.

In 125 ml of 1:1 $H_2O$/acetic acid is dissolved 5.0 gm (7.92 mmol) of N,N'-dibenzyloxycarbonyl-3'-(R)-aminomethyldihydrospectinomycin. To this solution is then added 2.7 g (39.6 mmol) of $NaNO_2$. An immediate evolution of $N_2$ is observed and the reaction is allowed to stir for 40 minutes. The solution is then poured into $H_2O$ (250 ml) and extracted with EtOAc ($2\times100$ ml). The combination extracts are then washed with saturated $NaHCO_3$ ($2\times100$ ml) and 10 percent aqueous $NH_4OH$ ($1\times100$ ml). The combined washes are backwashed with EtOAc. The combined organics are washed with brine and dried over $MgSO_4$. Removal of the solvent in vacuo affords 5.07 g of a white solid. The product is taken up in $CHCl_3$ and chromatographed on 300 g of silica, slurry packed in $CHCl_3$. The column is eluted as follows: 1 L 1 percent MeOH/$CHCl_3$; 5 L 2 percent MeOH/$CHCl_3$; 1 L 3 percent MeOH/$CHCl_3$; 4

L 5 percent MeOH/CHCl$_3$; 2 L 10 percent MeOH/CHCl$_3$. Each 50 ml fraction is analyzed by TLC. Pure fractions are pooled and concentrated in vacuo to afford the final product. In elution volume 2.7–3.95 L, 1.133 g of N,N'-dibenzyloxycarbonyl-homospectinomycin is obtained; $^{13}$C-NMR (d$_6$-Acetone) 189.0, 138.0, 129.1, 128.3, 99.1, 94.6, 78.0, 74.8, 67.2, 66.5, 65.8, 65.7, 37.1, 36.4, 31.5 and 22.2 δ; exact mass is calc'd for C$_{40}$H$_{62}$N$_2$O$_{11}$Si$_3$ (tri-TMS) 830.3661, found 830.3653. Also recovered from the column is 1.4 g of epoxide and 0.95 g of diol.

Utilizing a procedure similar to Example 1 above but substituting the appropriate protected and substituted aminomethyldihydrospectinomycin having the formula IV there is obtained the corresponding substituted and protected homospectinomycin having the formula IIa wherein $R_1$ and $R_3$ are as follows:

TABLE I

| | R$_1$ | R$_3$ |
|---|---|---|
| 1. | t-butoxycarbonyl | hydrogen |
| 2. | carbobenzyloxy | n-butyl |
| 3. | t-butoxycarbonyl | isopentyl |
| 4. | carbobenzyloxy | 2-propylbutyl |
| 5. | t-butoxycarbonyl | n-butoxy methyl |
| 6. | carbobenzyloxy | methoxy n-butyl |
| 7. | t-butoxycarbonyl | methoxymethyl |
| 8. | carbobenzyloxy | hexoxyisopropyl |
| 9. | t-butoxycarbonyl | dimethylaminoethyl |
| 10. | carbobenzyloxy | ethylpropylaminomethyl |
| 11. | t-butoxycarbonyl | dibromomethyl |
| 12. | carbobenzyloxy | 2-iodo-1-methylethyl |
| 13. | t-butoxycarbonyl | fluoro-n-butyl |
| 14. | carbobenzyloxy | 2-trichloroethyl |

EXAMPLE 2

Homospectinomycin (formula II$_b$: R$_3$ is methyl and R$_1$ is hydrogen)

Refer to Scheme B.

To a solution of 100 mg (0.16 mmol) of the N,N'-dibenzyloxycarbonylhomospectinomycin in 3 ml of methanol was added 100 mg of palladium black and 86 μl (1.6 mmol) of formic acid. The mixture was stirred 10 minutes at room temperature, filtered and concentrated in vacuo. The residue was dissolved in 2 ml of H$_2$O, treated with 0.35 ml (0.35 mmol) of 1N HCl and lyophilized to afford 65 mg (0.16 mmol, 100%) of homospectinomycin as a white solid: $^{13}$C-NMR (D$_2$O, CH$_3$CN internal reference) 189.9, 98.2, 94.2, 81.6, 70.9, 66.9, 62.3, 60.7, 59.3, 39.3, 37.5, 32.0, 31.5, 21.8; MS exact mass for M$^+$ of pentakistrimethylsilyl ether, C$_{30}$H$_{66}$N$_2$O$_7$Si$_5$ requires, 706.3716: found, 706.3739.

In a procedure for deprotection similar to the Example 2 above but substituting the appropriately substituted and protected homospectinomycin wherein R$_1$ is carbobenzyloxy having the formula IIa from TABLE I above there is obtained the corresponding deprotected but substituted homospectinomycin. Deprotection if R$_1$ is t-butoxycarbonyl is accomplished by treating with acid using appropriate conditions from those known in the art for deprotection. The deprotected compounds have the formula IIa wherein R$_1$ is hydrogen and R$_3$ is as follows:

TABLE II

| | |
|---|---|
| 1. | hydrogen |
| 2. | n-butyl |
| 3. | isopentyl |
| 4. | 2-propylbutyl |
| 5. | n-butoxy methyl |
| 6. | methoxy n-butyl |
| 7. | methoxymethyl |
| 8. | hexoxyisopropyl |
| 9. | dimethylaminoethyl |
| 10. | ethylpropylaminomethyl |
| 11. | dibromomethyl |
| 12. | 2-iodo-1-methylethyl |
| 13. | fluoro-n-butyl |
| 14. | 2-trichloroethyl |

EXAMPLE 3

N,N'-dibenzyloxycarbonylhomodihydrospectinomycin (formula II$_b$: R$_3$ is methyl and R$_7$ is benzyloxy carbonyl)

Refer to Scheme C

In 2 ml of absolute ethanol is dissolved 520 mg (0.85 mmol) of N,N'-dibenzyloxycarbonylhomospectinomycin. To this solution is then added 8.0 mg (0.21 mmol) of NaBH$_4$. The reaction is stirred for 2 hours and concentrated in vacuo. The residue is then partitioned between ethyl acetate and water. The water is acidified (pH=2) with 1N aqueous hydrochloric acid and the ethyl acetate is separated. The ethyl acetate is combined with a second ethyl acetate extract, of the aqueous solution, washed with brine and dried over magnesium sulfate. After filtering, the solvent is removed in vacuo to afford 536 mg of a white solid. The product is taken up in chloroform and chromatographed on 70 gm of silica, slurry-packed in chloroform. The column is eluted with 1 percent methanol in chloroform (1.5 L), followed by 2 percent methanol in chloroform. The desired product is found by TLC analysis of each 40 ml fraction. This afforded 218 mg of a white solid. This product is further purified by reverse phase chromatography using a C-18 packing. The column is eluted with 60:40 acetonitrile:water and the eluent is monitored at 257 nm. Each 20 ml fraction is analyzed by analytical HPLC and pure fractions are combined, concentrated in vacuo and extracted with EtOAc. After normal workup there is recovered 109 mg of the N,N'-dibenzyloxycarbonylhomodihydrospectinomycin as a white solid: $^{13}$C-NMR (d$_6$-Acetone) δ 138.5, 129.2, 128.5, 100.4, 96.4, 79.9, 75.8, 75.3, 75.0, 74.8, 67.3, 66.7, 65, 61.1, 60.9, 60.1, 58.0, 57.6, 38.1, 31.5, 30.8, and 22.6; exact mass calc'd for C$_{43}$H$_{72}$N$_2$O$_{11}$Si$_4$ (tetra-TMS) 904.4213, found 904.4222.

Utilizing a procedure similar to the Example 3 above but substituting the appropriately protected analog of homospectinomycin having the formula IIa there is obtained a protected homodihydrospectinomycin having the formula IIb wherein R$_1$ and R$_3$ are as follows:

TABLE III

| | R$_1$ | R$_3$ |
|---|---|---|
| 1. | t-butoxycarbonyl | hydrogen |
| 2. | carbobenzyloxy | ethyl |
| 3. | t-butoxycarbonyl | n-propyl |
| 4. | carbobenzyloxy | isopropyl |
| 5. | t-butoxycarbonyl | n-butyl |
| 6. | carbobenzyloxy | isobutyl |
| 7. | t-butoxycarbonyl | ht-butyl |
| 8. | carbobenzyloxy | isohexyl |
| 9. | t-butoxycarbonyl | hydroxymethyl |
| 10. | carbobenzyloxy | methoxyethyl |
| 11. | t-butoxycarbonyl | ethoxy-n-propyl |
| 12. | carbobenzyloxy | n-propoxy-1-butyl |
| 13. | t-butoxycarbonyl | isopropoxy methyl |
| 14. | carbobenzyloxy | dimethylaminoethyl |
| 15. | t-butoxycarbonyl | N—ethylpropylaminomethyl |
| 16. | carbobenzyloxy | dibromomethyl |
| 17. | t-butoxycarbonyl | 2-iodo-1-methylethyl |

TABLE III-continued

| | $R_1$ | $R_3$ |
|---|---|---|
| 18. | carbobenzyloxy | fluoro-n-butyl |
| 19. | t-butoxycarbonyl | trichloromethyl |

EXAMPLE 4

Homodihydrospectinomycin dihydrochloride (formula IIb: $R_1$ is carbobenzyloxy and $R_3$ is methyl)

Refer to Scheme D.

In 2 ml of methanol is dissolved 104 mg (0.168 mmol) of N,N'-dibenzyloxycarbonylhomodihydrospectinomycin. To this solution is added 100 mg of palladium black followed by 66 μl (1.68 mmol) of formic acid. The reaction is stirred for 20 minutes, filtered, and concentrated in vacuo to afford 78 mg of a white solid. The product is taken up in water and treated with 1 ml of 1N aqueous hydrochloric acid. The solution is frozen and lyophilized to afford 73 mg (100%) of the homodihydrospectinomycin dihydrochloride as a white solid: $^{13}$C-NMR (d$_6$-Acetone) δ 99.5, 97.0, 82.4, 76.6, 71.5, 67.1, 66.0, 62.4, 60.7, 59.7, 37.4, 31.9, 31.6, 29.8, and 22.3; exact mass calcd for $C_{27}H_{60}N_2O_7Si_4$ (tetra TMS) 636.3477, found 636.3422.

Utilizing a procedure for deprotection similar to the Example 4 above but substituting the appropriate protected homodihydrospectinomycin analog from TABLE III above for compounds wherein $R_1$ is carbobenzyloxy there is obtained the corresponding deprotected analog of homodihydrospectinomycin. Deprotection if $R_1$ is t-butoxycarbonyl is accomplished by treatment with acid using appropriate conditions from those known in the art for deprotection. The deprotected compounds have the formula IIb wherein $R_1$ is hydrogen and $R_3$ is as follows:

TABLE IV 1. hydrogen
2. ethyl
3. n-propyl
4. isopropyl
5. n-butyl
6. isobutyl
7. t-butyl
8. isohexyl
9. hydroxymethyl
10. methoxylethyl
11. ethoxy-n-propyl
12. n-propoxy-1-butyl
13. isopropoxy methyl
14. dimethylaminoethyl
15. N—ethylpropylaminomethyl
16. dibromomethyl
17. 2-iodo-1-methylethyl
18. fluoro-n-butyl
19. trichloromethyl

FORMULA

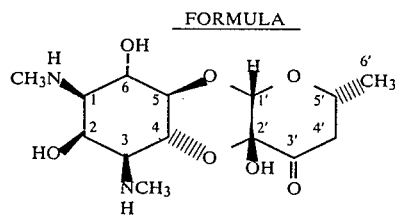

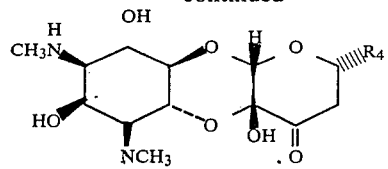
I'

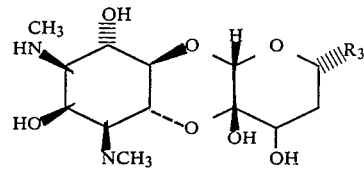
I2

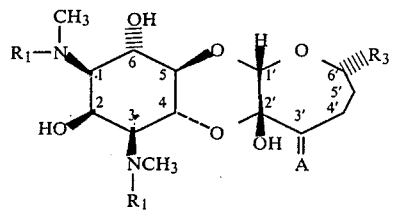
II

IIa

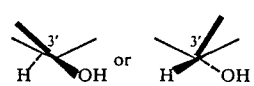
IIb (hereafter denoted as H in the structures and as α-H:β-OH or α-OH:B—H in the text)

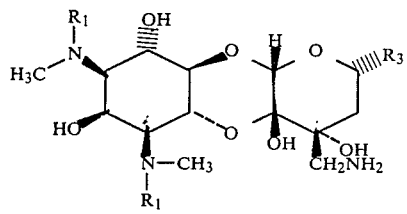
IV

SCHEME A

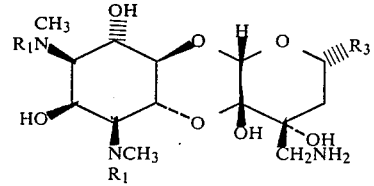
IV

 NaNO$_2$

+

V

-continued

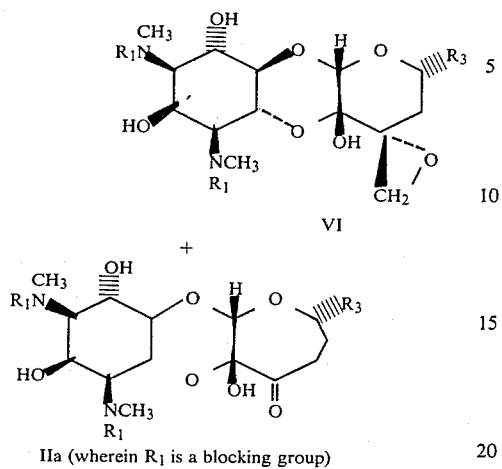

VI

+

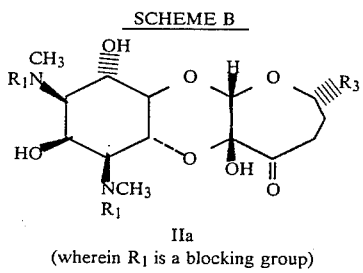

IIa (wherein $R_1$ is a blocking group)

SCHEME B

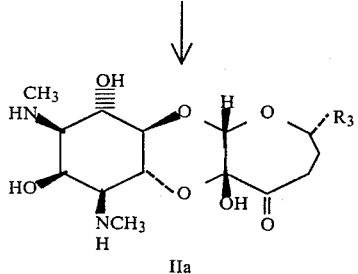

IIa
(wherein $R_1$ is a blocking group)

↓

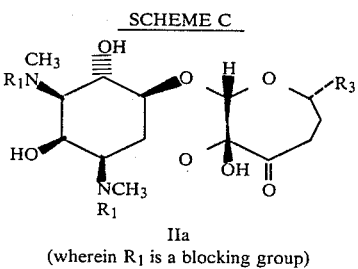

IIa

SCHEME C

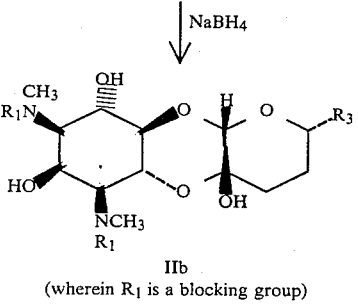

IIa
(wherein $R_1$ is a blocking group)

↓ NaBH₄

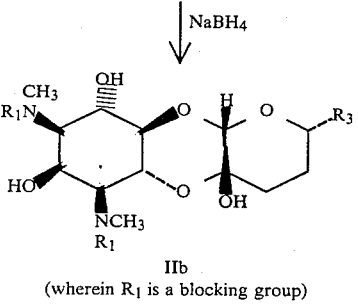

IIb
(wherein $R_1$ is a blocking group)

SCHEME D

-continued

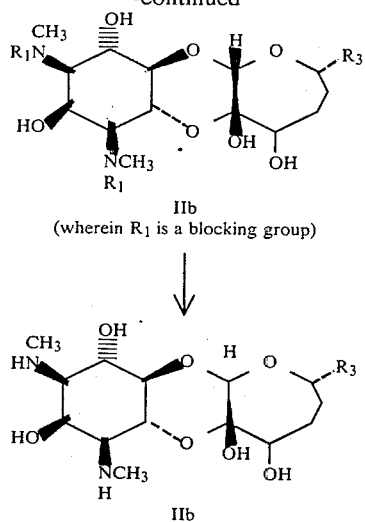

IIb
(wherein $R_1$ is a blocking group)

↓

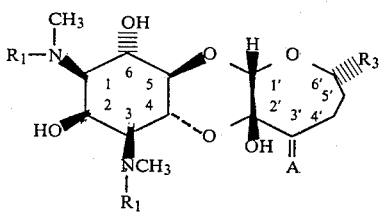

IIb

I claim:
1. A compound of formula II

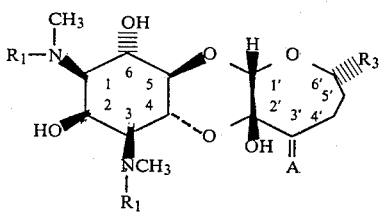

II wherein
$R_1$ is
  (a) hydrogen or
  (b) a blocking group; and
wherein
$R_3$ is
  (a) hydrogen
  (b) alkyl of 1 to 8 carbon atoms, inclusive,
  (c) —$R_{31}$—O—$R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
  (d) —$R_{31}NR_{33}R_{34}$, wherein $R_{31}$ is as defined above, wherein $R_{33}$ is hydrogen, alkyl of 1 to 6 carbon atoms, inclusive, and $R_{34}$ is hydrogen, alkyl of 1 to 6 carbon atoms, inclusive, or a blocking group with the proviso that if $R_{34}$ is not a blocking group, the sum of the number of carbon atoms in $R_{31}$ and the number of carbon atoms in whichever of $R_{33}$ or $R_{34}$ has the larger number of carbon atoms is less than or equal to 7, or
  (e) alkyl of 1 to 4 carbon atoms, inclusive, substituted with 1, 2 or 3 halogen atoms;
wherein
A is
  (a) =O or
  (b) α-H:β-OH; α-OH:β-H; and pharmacologically acceptable salts thereof.

2. A compound of claim 1 wherein $R_3$ is alkyl of from 1 to 8 carbon atoms, inclusive, A is =O or α-H:β-OH; α-OH:β-H; and $R_1$ is carbobenzyloxy.

3. A compound of claim 1 wherein $R_3$ is alkyl of from 1 to 8 carbon atoms, inclusive, A is =O or $\alpha$-H:$\beta$-OH; $\alpha$-OH:$\beta$-H; and $R_1$ is hydrogen.

4. A compound of claim 2 wherein A is =O such that the specific embodiment is N,N'-dibenzyloxycarbonylhomospectinomycin.

5. A compound of claim 3 wherein A is =O such that the specific embodiment is homospectinomycin, dihydrochloride.

6. A compound of claim 2 wherein A is $\alpha$-H:$\beta$-OH; $\alpha$-OH:$\beta$-H; such that the specific embodiment is N,N'-dibenzyloxycarbonylhomodihydrospectinomycin.

7. A compound of claim 3 wherein A is $\alpha$-H:$\beta$-OH; $\alpha$-OH:$\beta$-H; so that the specific embodiment is homodihydrospectinomycin dihydrochloride.

* * * * *

UNITED STATES PATENT OFFICE
CERTIFICATE OF CORRECTION

Patent No. 4,523,022         Dated June 11, 1985

Inventor(s) Richard C. Thomas

It is certified that error appears in the above-identified patent and that said Letters Patent are hereby corrected as shown below:

Column 9, line 35, "mre" should read --more--.
Column 11, line 42, "preparation" should read --preparing--.
Column 12, line 17, "as" should read --an--.
Column 16, Formula I' line 3, "OH " should be --OH --.

Column 16, IIb, lines 31-32, " [structure] or [structure] "

should read -- [structure] or [structure] --

UNITED STATES PATENT OFFICE
CERTIFICATE OF CORRECTION

Patent No. 4,523,022                    Dated June 11, 1985

Inventor(s) Richard C. Thomas

It is certified that error appears in the above-identified patent and that said Letters Patent are hereby corrected as shown below:

Column 17, line 17, " 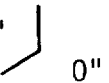 should read -- 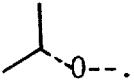 --.

Column 17, line 49, "  should read -- 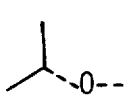 --

Column 17, lines 63-64, " 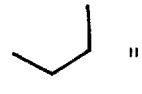 " should read -- 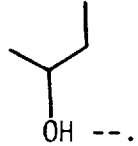 --.

Signed and Sealed this

Twenty-fifth Day of March 1986

[SEAL]

Attest:

DONALD J. QUIGG

Attesting Officer       Commissioner of Patents and Trademarks